United States Patent [19]

Kenny

[11] 4,248,237

[45] Feb. 3, 1981

[54] CARDIAC PACEMAKERS

[75] Inventor: John Kenny, Sawbridgeworth, England

[73] Assignee: Needle Industries Limited, Studley, England

[21] Appl. No.: 884,966

[22] Filed: Mar. 9, 1978

[51] Int. Cl.³ .............................................. A61N 1/36
[52] U.S. Cl. .................................................. 128/419 P
[58] Field of Search ....... 128/419 P, 419 PG, 419 PS, 128/419 B, 419 C, 419 E

[56] References Cited

U.S. PATENT DOCUMENTS

| | | |
|---|---|---|
| 3,760,332 | 9/1973 | Berkovits et al. ................. 128/419 P |
| 3,842,842 | 10/1974 | Kenny et al. ...................... 128/419 P |
| 3,871,382 | 3/1975 | Mann ................................. 128/419 P |
| 3,888,260 | 6/1975 | Fischell ............................. 128/419 P |
| 3,924,639 | 12/1975 | Hess ................................... 128/419 P |

FOREIGN PATENT DOCUMENTS 1219017  1/1971  United Kingdom ................. 128/419 P

*Primary Examiner*—William E. Kamm
*Attorney, Agent, or Firm*—Alexis Barron

[57] ABSTRACT

A case for an implantation in a human or animal body. The case comprises a rigid plastics substrate which defines a chamber and a platinum skin arranged to overlie the substrate, the skin being formed in two or more pieces welded together—for instance by electron beam welding—to form a hermetically sealed case. The platinum skin should be from 0.1875 mm to 0.5 mm thick and is biocompatible, rendering the case suitable for implanting and containing a power pack and electronic package for a cardiac pacemaker.

12 Claims, 9 Drawing Figures

CARDIAC PACEMAKERS

BACKGROUND OF THE INVENTION (a) Field of the Invention

This invention relates to a cardiac pacemaker suitable for implantation in a human or animal body as a part of a complete cardiac pacemaker system. A complete cardiac pacemaker system may additionally comprise a plug and socket connector (such as is described and claimed in my co-pending application Ser. No. 884,830 filed on the same day as this application in my name alone and entitled "Plug and Socket Connectors," the entire disclosure of which is incorporated herein by reference) and an electrode catheter to carry electric pulses to the heart (such as is described and claimed in my co-pending application Ser. No. 884,967, now abandoned, filed on the same day as this application in my name alone and entitled "Electrode Catheter," the entire disclosure of which is incorporated herein by reference).

(b) Description of the Prior Art

In a cardiac pacemaker system, the implanted pacemaker itself, which supplies pulses at regular intervals to stimulate the heart via an electrode catheter, must have a long and reliable life because surgery is required to correct any fault and of course in an extreme case the consequence of a pacemaker failure may be fatal. It is therefore most important that the case within which the power source and electronic components for generating the train of electric pulses are housed must be totally hermetically sealed and resistant to the body fluids present at the site of implantation. Cases have been made of metals such as stainless steel and titanium, but in the environment within a body, these metals suffer from electrolytic corrosion, especially if used as an electrode for return electric current. This corrosion may effect the bio-compatibility after a period of time. Plastics materials, such as epoxy resins, have been employed for implantation pacemaker cases, but moisture from the body can cause the resins to swell, leading eventually to cracking. Plastics cases thus have a typical life of 3 years. Polypropylene is another plastics material currently often employed for implant cases, but moisture tends to diffuse through polypropylene over a period of time and this can lead to premature failure of the contained electronic components. Also, when using a plastics material, it is necessary to provide a contact on the outer surface of the case to form an "earth return" for the electric circuit and this also can cause problems. In the first place, electrolytic corrosion may take place, but also if the plastics material is liable to change its physical structure or dimensions over a period of years, the security of attachment of the contact pad and the hermetic seal of a wire leading thereto through the case may fail.

In view of all of the above difficulties, there has been no commercially successful implant case which has been entirely free of problems for the life of the contained components. It has been appreciated that because platinum is relatively inert in a human or animal body and is bio-compatible, it would be a suitable material for a case, but in view of the cost of platinum it is not practical to make a case thereof. Platinum with a sufficient degree of purity to ensure bio-compatibility is relatively soft and this means that a case made of platinum must have a considerable wall thickness, thus putting up the cost yet more. Moreover, the weight of a sufficiently strong case can cause difficulties when the case has been implanted.

OBJECTS OF THE INVENTION

It is a principal object of this invention to provide a construction of pacemaker casing which overcomes the problems mentioned above relating to the known casings. It is thus an object of this invention to provide a pacemaker casing which can be implanted in a body for many years without deterioration, and without the electronic package therewithin becoming contaminated by the ingress of moisture.

It is a further object of this invention to provide a pacemaker casing which is relatively simple and cheap to construct, and lends itself to production in numbers.

It is also an object of this invention to provide a pacemaker system incorporating a casing which is resistant to the body fluids at the site of implantation, is reliable and can be left implanted for many years.

SUMMARY OF THE INVENTION

In accordance with these and other objects, there is provided a case for implantation in a human or animal body, which case comprises a rigid substrate of a plastics material which substrate defines a chamber, and a skin of platinum fitted over said substrate so as to be supported thereby, the skin being formed of at least two pieces of platinum of thickness in the range of from 0.1875 mm to 0.5 mm and welded together along mating edges to form a hermetically-closed case surrounding and supported by said rigid substrate.

According to another aspect of this invention, there is provided a pacemaker system, comprising a power source, an electronic package driven by said power source to generate timed electrical pulses, a case for implantation in a body and containing said power source and said electronic package, said case comprising a rigid plastics substrate of a plastics material and a skin of platinum fitted over said substrate so as to be supported thereby, the skin being formed of at least two pieces of platinum welded together along mating edges to form a hermetically-closed chamber, and a socket member, the pacemaker system further comprising an electrode catheter having a proximal end and a distal end, there being a plug member fitted on said proximal end for co-operation with said socket member of said case and an electrode at said distal end.

BRIEF DESCRIPTION OF THE DRAWINGS

In order that the invention may better be understood, it will now be described in greater detail, and a specific embodiment thereof given by way of example, reference being made to the accompanying drawings. In the drawings.

DETAILED DESCRIPTION OF THE PREFERRED ARRANGEMENTS

As mentioned above, it has been found that platinum is essentially inert when implanted in a human or animal body, even if in the body for a considerable number of years, and very little—if any—corrosion, pitting or other deterioration takes place. Whereas a case made from thick-walled platinum of a strength sufficient to protect contained electronics would be prohibitively expensive and very heavy, the strength of the case of this invention is provided by a plastics material substrate which supports only a skin of platinum. Typically, the skin may be from 0.1875 mm to 0.25 mm thick and preferably is 0.25 mm thick. In this way, the high strength and low weight of a plastics construction can be combined with the corrosion resistance of platinum, and moreover the platinum can provide the "earth return" electrode for the casing.

Though the rigid plastics material substrate could be in the form of a framework for supporting the platinum skin, it is preferred for the substrate to have continuous walls defining a closed chamber. Such a substrate advantageously is moulded from polypropylene. Preferably, the substrate is in the form of two mating parts which may be mated after the required power source and electronic package have been located therewithin. Preferably also the skin of platinum is in two preformed parts which respectively fit over the two parts of the substrate when mated, with the joint between the two platinum parts overlying the joint between the two parts of the substrate. The two parts of the platinum skin either may overlap slightly, or may more simply abut, as is more appropriate for the welding technique to be employed to join the two parts together. Advantageously, an electron beam butt-welding technique is used.

It will be appreciated that no separate contact pad need be provided with a case of this invention to serve as an earth return, because the platinum skin itself may perform this function. However, a suitable connector must be provided for an electrode catheter or similar device to carry the electric pulses to the site of stimulation—and normally the heart. To this end, it is preferred for the case of this invention to incorporate a socket member of a plug and socket electrical connector, the catheter carrying a plug member which may be fitted into the socket member. Conveniently, the socket member comprises a ceramic body defining a bore for receiving the plug member, the ceramic body having a metallic flange around the opening to the bore. By providing an aperture in the platinum skin, corresponding in shape and position to the metallic flange, the skin can be welded to the flange so as to form a hermetic seal therewith. The flange can be made of platinum, but by careful design, titanium can be used if the flange is not, or is only to a very small extent, exposed to the body fluids.

Figure 1:
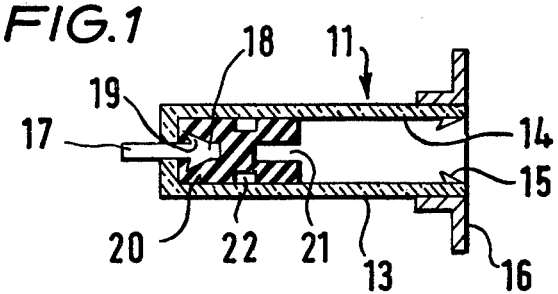
FIG. 1 is a cross-sectional view through an electrical socket member used in a pacemaker casing of this invention.
Figure 2:
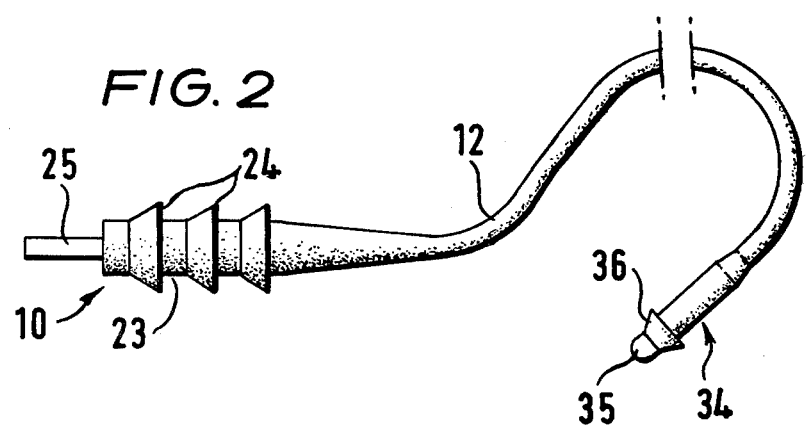
FIG. 2 is a side view of an electrode catheter including a plug member for use with the socket member shown in FIG. 1.
Figure 3:
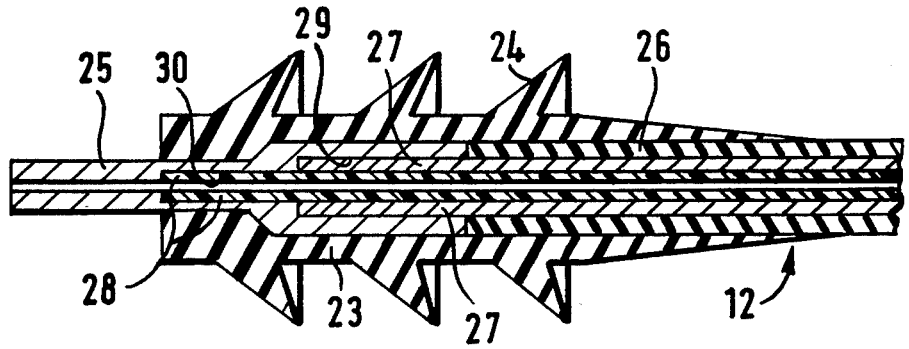
FIG. 3 is a cross-sectional view, but on an enlarged scale, through the plug member shown in FIG. 2, as fitted to an electrode catheter.
Figure 4:
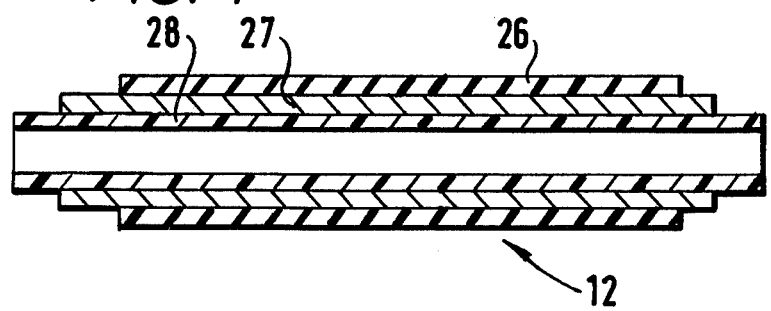
FIG. 4 is a cross-sectional view through part of an electrode catheter of FIG. 2.

Referring initially to FIGS. 1 to 3, there is shown a plug and a socket connector intended for connecting an electrode catheter of a cardiac pacemaker system to a pacemaker casing. The connector comprises a plug member 10 and a socket member 11, the plug member 10 being moulded directly on the end of the electrode catheter 12 and the socket member 11 being adapted for incorporation in the casing of the pacemaker itself.

The socket member 11 (FIG. 1) comprises a main body 13 made from a ceramic material and defining a blind circular bore 14. An inwardly directed annular rib 15 is provided within the bore 14, spaced slightly from the open end thereof and upstanding from the wall defining the bore by about 0.1 mm. A circular metallic flange 16 (for instance of titanium) is provided on the ceramics body portion 13 around the open end of the bore 14 during the manufacture of the socket member, so that the flange 16 is hermetically bonded to the main body 13. Similarly, a conducting contact 17 is provided through the blind end wall of the main body 13 so as to project into the bore 14. The contact is conveniently of platinum, and is also hermetically sealed to the main body. Within the bore 14, the contact 17 has an enlarged head 18, provided with barbs 19 directed towards the blind end of the bore. Located within the bore 14 is a block 20 of relatively soft, resilient conducting silicone rubber material, loaded with carbon particles to render the block electrically conducting. The block 20 is generally of circular cross-section to fit closely within the bore 14, and has a circular recess 21 opening co-axially towards the open end of the bore 14. A second co-axial recess is provided for receiving the head 18 of the contact 17, the block 20 being deformed to fit over the head and engage with the barbs 19, thereby making a good electrical connection therebetween. An annular channel 22 is provided partway between the ends of the block 20 of conducting silicon rubber material.

The conducting silicone rubber material is known per se and comprises relatively soft, resilient silicon rubber which has been loaded with carbon black. Such material displays reasonable electrical conductivity, though the resistance offered depends to some extent upon the degree of compression of the material. A typical material is that known as Dow-Corning Q4-1602 Silastic.

The plug member 10 (FIGS. 2 and 3) comprises a body portion 23 of circular cross-section and is provided with three annular ribs 24, each having the general cross-sectional shape of a barb directed generally away from the free end of the plug member 10. The body portion 23 is moulded from insulating silicone rubber, and is thus flexible, relatively soft and resilient. The material is similar to that of the block 20, except that it has not been loaded with carbon black; as such the material displays excellent insulating properties. A typical material for this purpose is that known as Dow-Corning MDX-4-4210 Clean-Grade Elastomer. The body portion 23 is moulded around a metal spigot 25, which projects from the free end of the body portion for connection with the socket member of FIG. 1. The diameter of the spigot 25 should be slightly greater than that of the recess 21 when the block of silicone rubber is located in the bore 14 of the socket member 11.

As shown in FIG. 3, the body portion 23 is moulded directly on to an electrode catheter 12, which is described in detail below. The catheter 12 includes an outer insulating silicone rubber protective sleeve 26, conductors 27 and a plastics core 28. The spigot 25 is shaped to receive in a first counterbore 29 the conductors 27, to make electrical connection within, and in a second, smaller counterbore 30 the plastics core 28. The body portion 23 bonds during the moulding operation to the sleeve 26, and if required the spigot 25 can lightly be crimped on the conductors 27 to ensure a reliable electrical connection thereto.

In use, when the plug member 10 is fitted into the socket member 11, the spigot 25 enters the recess 21 in the block 20 of conducting silicone rubber located within the bore 14 and makes an electrical connection therewith. By arranging the diameter of the recess 21 to be of slightly smaller size than that of the spigot 25, the rubber is compressed and resiliently urged into engagement with the spigot, as the spigot enters the recess 21 and a good electrical connection is thereby achieved. The annular channel 22 allows the rubber to distort and deform as required to allow accommodation of the spigot 25 in the recess 21. The annular ribs 24, shaped as barbs, allow the body portion 23 of the plug member easily to enter bore 14 of the ceramic body 16 but restrain withdrawal of the plug member owing to their barb-like shape. The rib 24 nearest the catheter 12 rides over and engages behind rib 15 of the socket member 11, and further assists in the retention of the plug member within the socket member. Moreover, the ribs 24 of the plug member 10 effect a hermetic seal between the body portion 23 of the plug member and the main body 13 of the socket member, whereby the electrical connection between the spigot 25 and the block 20 of conducting silicone rubber material is isolated from the surrounding environment.

Figure 5:
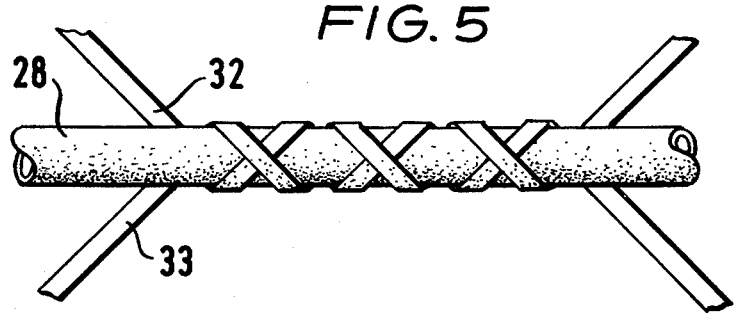
FIG. 5 is a diagram showing the fabrication of the catheter of FIG. 4.

Referring now to FIGS. 3 to 6, there is shown an electrode catheter 12 intended for use in a cardiac pacemaker system, connectible by means of the plug and socket connector described above to a pacemaker casing, and having an electrode for heart stimulation at its distal end. The catheter comprises a flexible, hollow core 28 of insulating plastics material such as polypropylene over which is laid a plurality of carbon-fibre monofilament conductors 27, each of approximately 10μ diameter. The carbon-fibre monifilament conductors 27 are assembled together into two groups 32 and 33 each containing several hundred such monofilaments randomly-oriented—and typically from 200 to 1000—and the two groups are then wave-wound around the core 28 as shown in FIG. 5. In this way, the groups are interwoven around the core 28 to form an open net-like tubular structure extending along the plastics core 28.

Extruded over the core 28 carrying the wave-wound groups of monofilament conductors 27 is a protective, insulating sleeve 26, of insulating silicone rubber material. By extruding the silicone rubber sleeve 26 directly as a tube over the carbon-fibre monofilament conductors 27, the sleeve is moulded around the groups of filaments as well as the filaments themselves such that they are partially embedded in the sleeve. In this way, the sleeve serves to retain the conductors 27 in the required position, as well as protecting the conductors against damage and insulating the conductors from the surroundings.

The electrode catheter described above has a relatively low impedance with good flexibility, whilst displaying excellent torsional rigidity (owing to the plastics core 28) allowing the catheter to be inserted where required within an animal or human body. The silicone rubber sleeve is virtually inert and is essentially biocompatible within human or animal bodies.

The catheter may be terminated at the proximal end with the plug described above, or instead may be terminated with one of the more usual plug or other connectors used with known cardiac pacemaker systems or other equipment in which an electrode catheter must be inserted or implanted in a body. The distal end of the catheter should be terminated in an appropriate manner for the intended use of the catheter, and such terminations—for instance for cardiac stimulation—are well known in the art.

Figure 6:
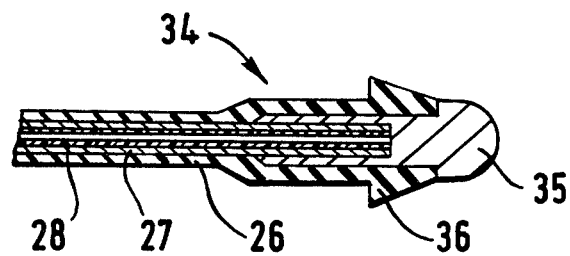
FIG. 6 is a cross-sectional view, but on an enlarged scale, through the distal end portion of the electrode catheter shown in FIG. 2.

FIG. 6 shows the electrode 34 provided at the distal end of the electrode catheter. This electrode comprises a platinum tip 35 having a rounded free end, there being an axial bore extending into the tip from its other end. In this bore are received the plastics core 28 and the carbon-fibre conductors 27 such that the conductors are connected electrically to the tip 35. The silicon rubber sleeve 26 is moulded directly over part of the tip 35 so as to insulate the greater part thereof and to hold the tip on the core and conductors. A silicone rubber flange 36 is provided at the end of the sleeve 26 so as to assist retention of the electrode in the required position.

Figure 7:
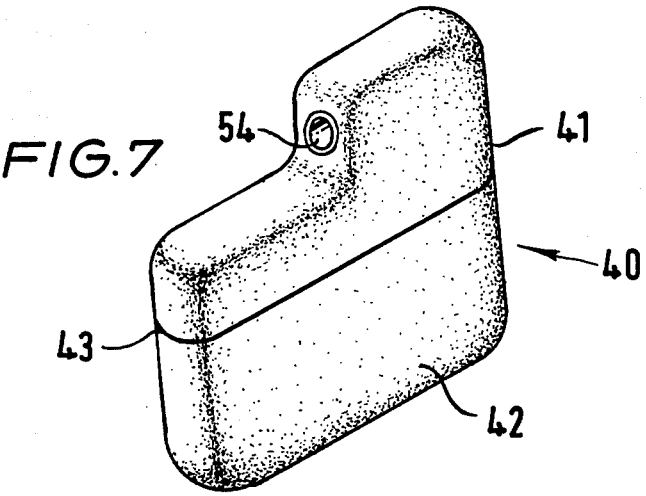
FIG. 7 is a perspective view of a cardiac pacemaker casing constructed in accordance with this invention and incorporating the socket member shown in FIG. 1.
Figure 8:
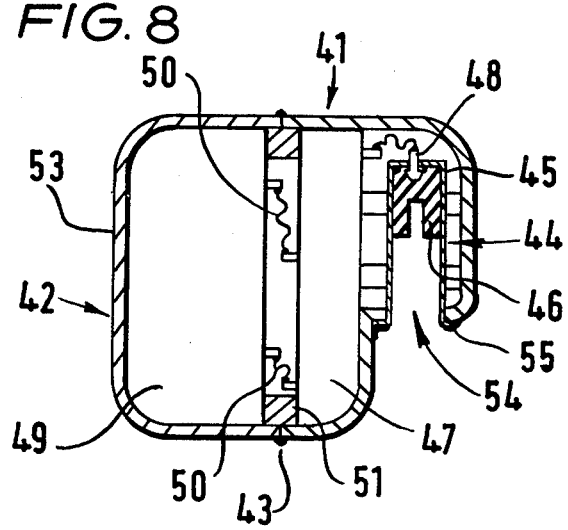
FIG. 8 is a cross-section through the pacemaker casing of FIG. 7.
Figure 9:
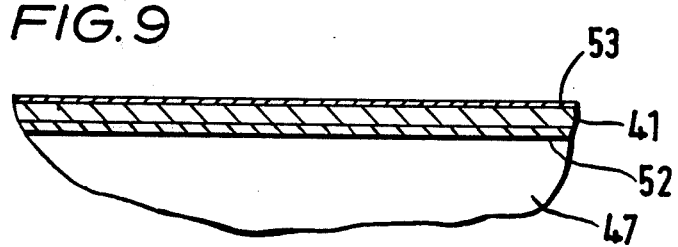
FIG. 9 is a cross-section through the wall of the pacemaker casing of FIG. 7, but on an enlarged scale.

FIGS. 7 to 9 show a cardiac pacemaker implant case 40, embodying a socket member generally similar to that shown in FIG. 1 and for use with a catheter electrode having a plug member as shown in FIG. 3.

The case for the pacemaker comprises two separate moulded plastics chamber parts 41 and 42, which mate together at 43 to define a complete chamber. Part 41 is fitted with a socket member 44, comprising a ceramic body 45 defining a bore in which is located a conducting silicon rubber block 46, connected to an electronic package 47 contained within chamber part 41 by means of contact 48 extending through the ceramic body 45. Within the chamber part 42 is a battery pack 49, connected to the electronic package 47 by means of wires 50. A continuous ring 51 of resilient silicone rubber material is positioned between the electronic package 47 and the battery pack 49 so as to urge the package and pack 47 and 49 respectively apart, into firm engagement with the associated chamber parts 41 and 42. The ring 51 moreover is engaged with the chamber parts 41 and 42 immediately under the mating region 43 of the chamber parts. If required, as shown in FIG. 9, a layer 52 of silicon rubber can be provided between the inner wall of a chamber part and the package or pack therewithin. The two chamber parts 41 and 42 can be glued together once all the components have been assembled therewithin, by means of an adhesive selected for the plastics material of the chamber parts. For instance, the parts can be of an epoxy resin, and a similar region used for glueing the parts together.

The entire moulded plastics chamber parts 41 and 42 are covered by a platinum skin 53, also formed in two separate parts which abut in the mating region 43 of the two chamber parts. The skin is shaped from platinum sheet of about 0.25 mm thickness, so as to fit closely over the chamber parts. An aperture 54 is provided in the skin around the opening into the bore of the socket member 44. The abutting edges of the two separate parts of the skin 53 are welded together by an electron beam welding technique and the skin is also welded around the aperture 54 to a metal flange 55 around the socket member 44 by the same technique, whereby a continuous, hermetical seal is formed around the entire casing.

The two parts of the platinum skin conveniently are formed by a deep drawing operation from a flat sheet of platinum, using the chamber parts themselves as the male drawing tool. Pure platinum is relatively soft and lends itself to such a forming operation, especially when in a relatively thin sheet, particularly because the material displays virtually no spring-back. However, the skin could be formed separately and then fitted to the assembled chamber parts prior to the welding operation.

An electrical connection must be provided to the platinum skin, to allow a current return from the distal end of a catheter used with the pacemaker case. Conveniently, this is effected by means of the flange 55 of the socket member 44, connected internally back to the electronic package 47 within chamber part 41.

In use, an appropriate electrode catheter fitted with a plug member at its proximal end for insertion into socket member 44 is introduced into the body so that the distal end is within the heart where stimulation is required, and the proximal end is adjacent the site of implanting of the pacemaker case. If a catheter such as is described above is used, excellent torsional control of the distal end can be achieved by operation—and principally rotation—of the proximal end during positioning of the distal end. Next, the plug member 10 of the catheter is inserted into the socket 40 of the pacemaker casing, and the pacemaker is positioned suitably at the implantation site, whereafter the surgery is completed in the usual way.

It is found that the platinum skin, even though serving as a contact for the earth return, is not prone to corrosion or other deterioration, for platinum proves to be virtually inert within the environment of a human or animal body at the usual sites of implantation. Thus the life of the implanted pacemaker will be dictated by the battery pack 49, rather than by the life of the pacemaker casing or the life of the electrode catheter—and battery packs are currently being produced which should call for preventative replacement only every 5 years, even though the actual life may be yet longer.

What is claimed is:

1. A case for implantation in a body, which case comprises a rigid supporting substrate of a plastics material, which substrate defines a chamber, and a skin of platinum fitted over said substrate and forming the outermost surface of the case, the skin being formed of at least two pieces of platinum, the thickness of which pieces is 0.1875 mm to 0.5 mm, the pieces of platinum being welded together along mating edges to form a hermetically-closed case surrounding and being supported by said substrate.

2. A case as claimed in claim 1, in which the thickness of said platinum skin is 0.1875 mm to about 0.25 mm.

3. A case as claimed in claim 1 in which said rigid substrate of plastics material is in the form of two mating parts each of which has solid walls, and two parts being mated to define a closed chamber in which are located a power source and an electronic package powered by said power source to generate timed electrical pulses.

4. A case as claimed in claim 3, in which said skin of platinum is in two pre-formed parts which respectively fit over the two parts of the substrate when mated, the joint between the two platinum parts overlying the joint between the two parts of the substrate.

5. A case as claimed in claim 1, in which the parts of the platinum skin are joined by a butt weld.

6. A case as claimed in claim 1, in which a socket member of a plug and socket electrical connector is provided in said case to allow connection of an electrode catheter carrying a plug member of said plug and socket connector, said socket member comprising a ceramic body defining a bore for receiving the plug member and a metallic flange around the opening to the bore, said platinum skin being formed with an aperture corresponding in shape and position to said metallic flange, and said skin being welded to said flange so as to form a hermetic seal therewith.

7. A case according to claim 3, 4, 5 or 6 in which the thickness of said platinum skin is 0.1875 mm to about 0.25 mm.

8. A case according to claim 7 in which said thickness is about 0.25 mm.

9. A cardiac pacemaker system for implantation in a body, comprising an electrode catheter having a proximal end and a distal end, a plug member having an insulating body portion and a projecting conducting spigot being provided at said proximal end and an electrode for stimulating the heart being provided at said distal end, and a cardiac pacemaker case comprising a rigid substrate of a synthetic resinous plastic material in the form of two mating parts, each of which has solid walls, said two parts being mated to define a closed chamber, a power source, an electronic package to generate timed electrical pulses, said power source and said electronic package being located within said closed chamber, a socket member for receiving said plug member provided in one of said parts to allow the connection of the proximal end of the electrode catheter thereto, the socket member comprising a ceramic body defining a bore for sealingly receiving said plug member, a block of resilient conducting silicone rubber material located within said bore and having a recess for receiving the spigot of the plug member, the recess having a smaller cross-sectional dimension than that of the spigot, the socket member further comprising an electrical contact provided through the wall of the socket member defining the bore and being electrically connected to said electronic package, said contact making electrical connection with the block of conducting silicone rubber material within the bore, and a metallic flange surrounding the opening to said bore, said case further comprising a skin of platinum fitted over and supported by said rigid substrate, said skin having a thickness of from 0.1875 mm to 0.5 mm and being formed in two parts, each of which fits respectively over said two mating parts of said rigid substrate and one of said parts of the platinum skin having an aperture corresponding in shape and position to said metallic flange of the socket member, the two parts of the platinum skin being welded together and said metallic flange being welded to said one part of the platinum skin so as to form a hermetically sealed case.

10. A pacemaker system as claimed in claim 9, in which said electrode catheter comprises a flexible core of insulating plastics material, a plurality of conducting carbon-fibre monofilaments laid over the core to lie along the length thereof from the proximal end to the distal end, and a flexible sleeve of bio-compatible insulating material covering the carbon-fibre monofilaments.

11. A cardiac pacemaker system for implantation in a body as claimed in claim 9 or 10 in which the thickness of the pieces of platinum forming the skin is 0.1875 mm to about 0.25 mm.

12. A cardiac pacemaker system according to claim 11 in which said thickness is about 0.25 mm.

* * * * *

UNITED STATES PATENT AND TRADEMARK OFFICE
CERTIFICATE OF CORRECTION

PATENT NO. : 4,248,237

DATED : February 3, 1981

INVENTOR(S) : John Kenny

It is certified that error appears in the above—identified patent and that said Letters Patent is hereby corrected as shown below:

Column 7, line 54      "and" should read --said--.

Signed and Sealed this

Eighteenth Day of August 1981

[SEAL]

Attest:

Attesting Officer

GERALD J. MOSSINGHOFF

Commissioner of Patents and Trademarks